United States Patent [19]

Lewis et al.

[11] 4,361,142
[45] Nov. 30, 1982

[54] KNEE ORTHOSIS AND JOINT CONSTRUCTION THEREFOR

[75] Inventors: Jack L. Lewis, Evanston; Carl M. Patrnchak; William D. Lew, both of Chicago, all of Ill.; George T. Shybut, Brookline, Mass.

[73] Assignee: Northwestern University, Evanston, Ill.

[21] Appl. No.: 294,445

[22] Filed: Aug. 20, 1981

[51] Int. Cl.³ ............................................. A61F 3/00
[52] U.S. Cl. ..................................... 128/80 C; 128/88
[58] Field of Search ................. 128/80 C, 80 F, 80 R, 128/87 R, 88; 3/22

[56] References Cited

U.S. PATENT DOCUMENTS

| | | | |
|---|---|---|---|
| 3,779,654 | 12/1973 | Horne | 128/80 C X |
| 3,823,424 | 7/1974 | May | 3/22 |
| 3,885,252 | 5/1975 | Nakajima | 128/80 C X |
| 3,901,223 | 8/1975 | May | 128/80 F |
| 4,241,730 | 12/1980 | Helfet | 128/80 C |

Primary Examiner—John D. Yasko
Attorney, Agent, or Firm—Tilton, Fallon, Lungmus

[57] ABSTRACT

An orthotic joint, and the orthosis with which it is used, for the protective treatment of ligamentous injuries or deficiencies, or as a supplement to total joint replacement. The joint includes coacting guide members that are both slidable and pivotal with respect to each other and, when assembled and supported in pairs on opposite sides of a patient's knee, allow freedom of movement of the knee except for those movements that would normally be controlled by the ligament or ligaments requiring protection. An arrangement of straps connect each pair of guide members and are tensioned (and untensioned) in sequence to perform operations in conjunction with the articulating surfaces of the members that would otherwise be demanded from the protected ligament(s). The orthosis includes a system of interfacial elements and suspension elements that engage the upper and lower leg portions and effectively maintain the orthotic joints in proper positions to restrain abnormal knee movements or, in the case of prosthetic joint replacement, to prevent movements that do not conform with the prescribed action of the replaced joint.

36 Claims, 19 Drawing Figures

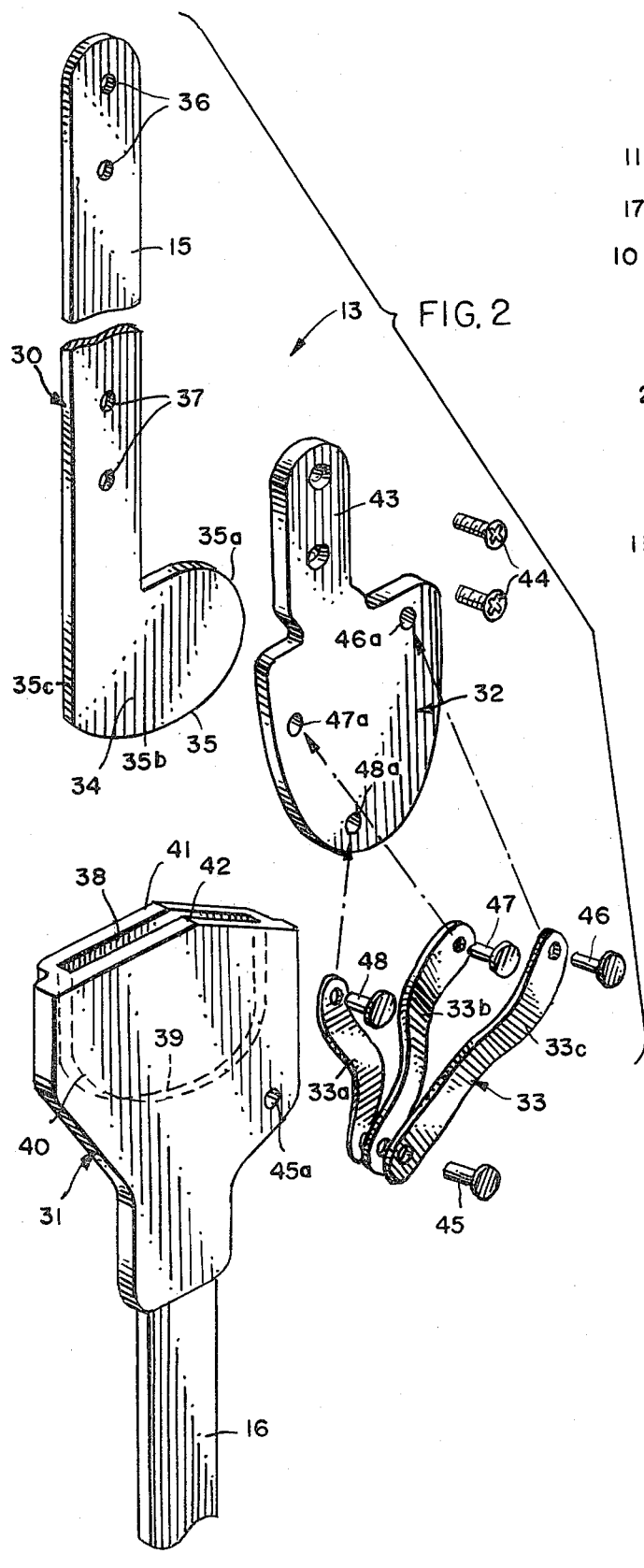
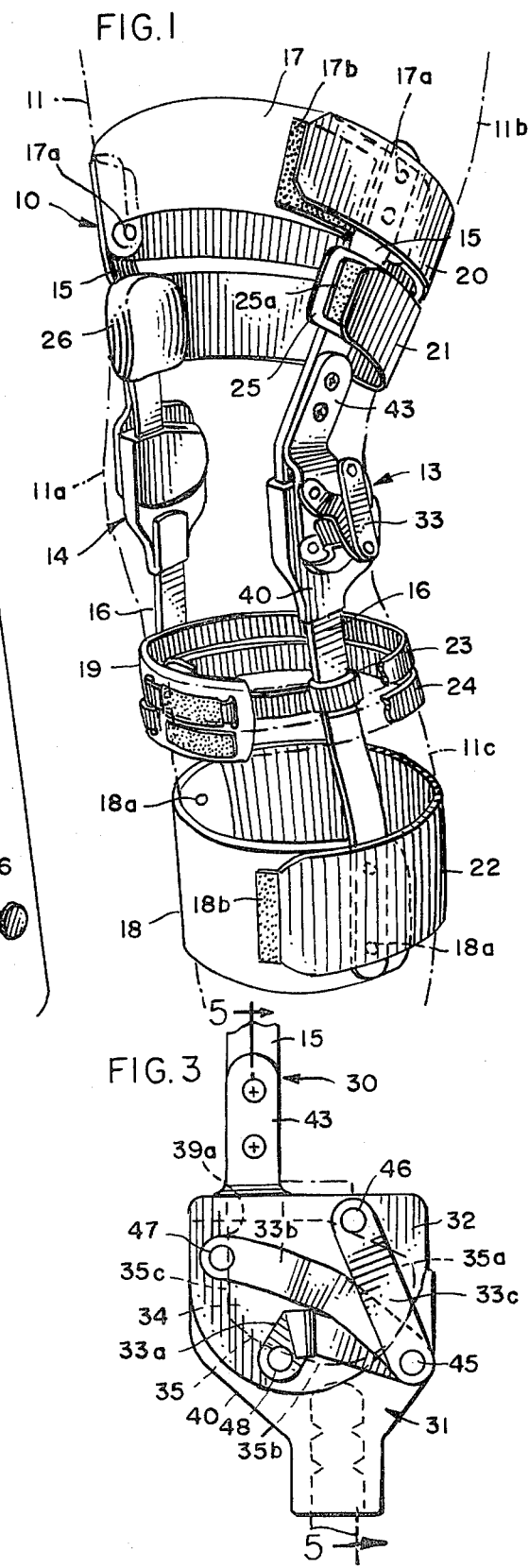
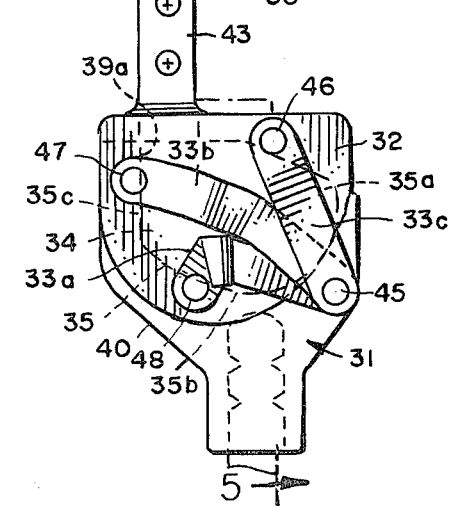

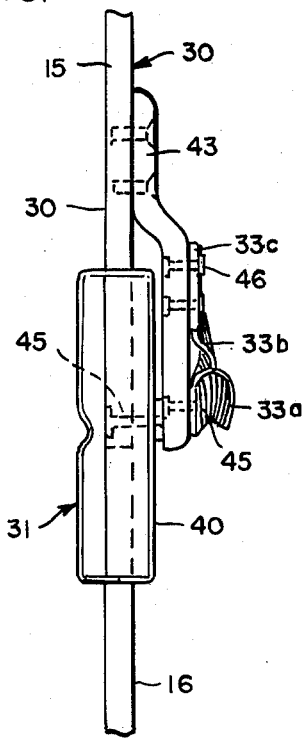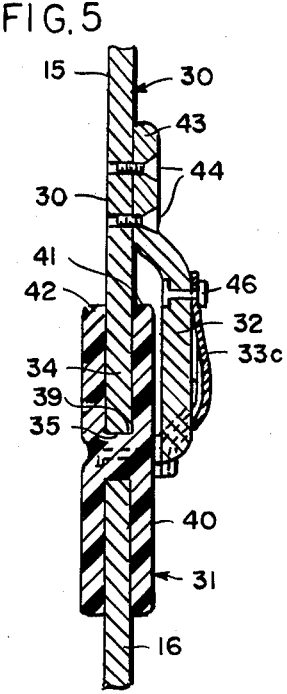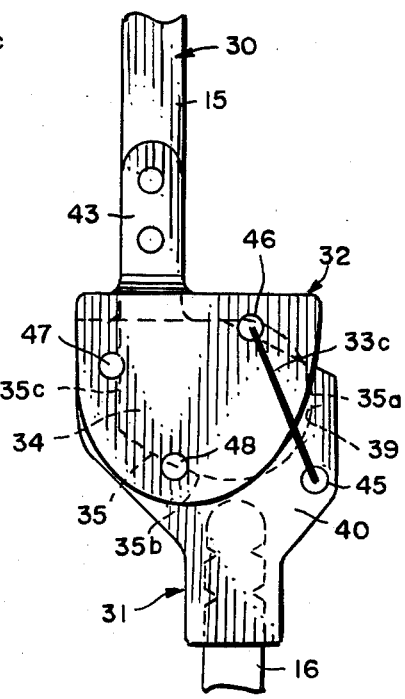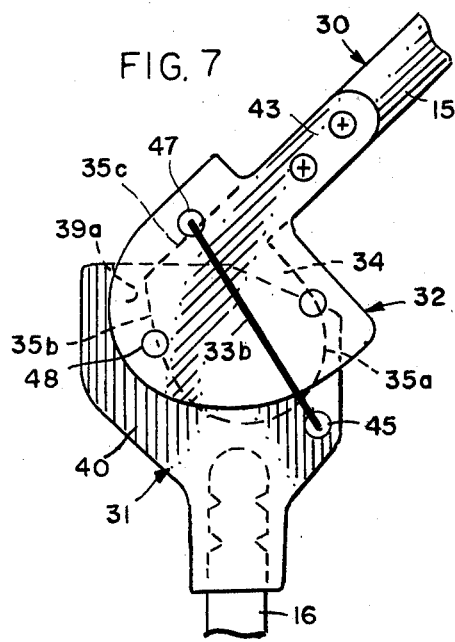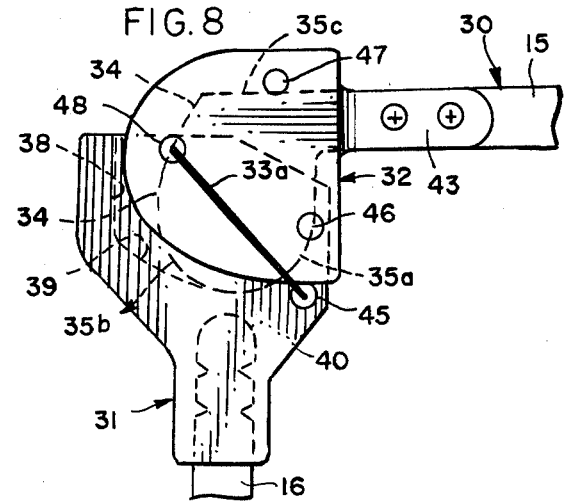

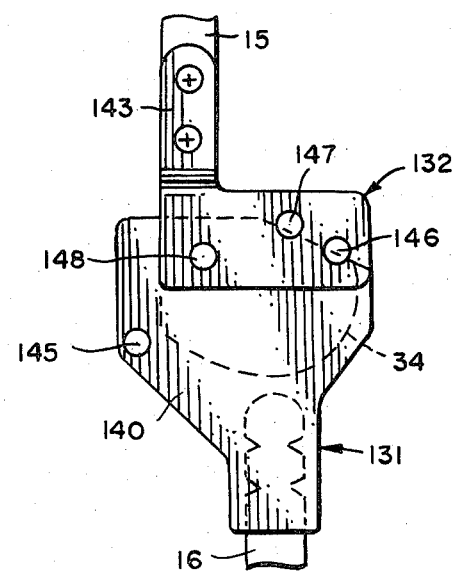
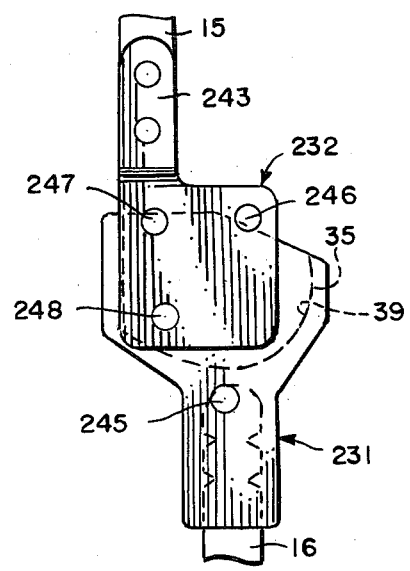
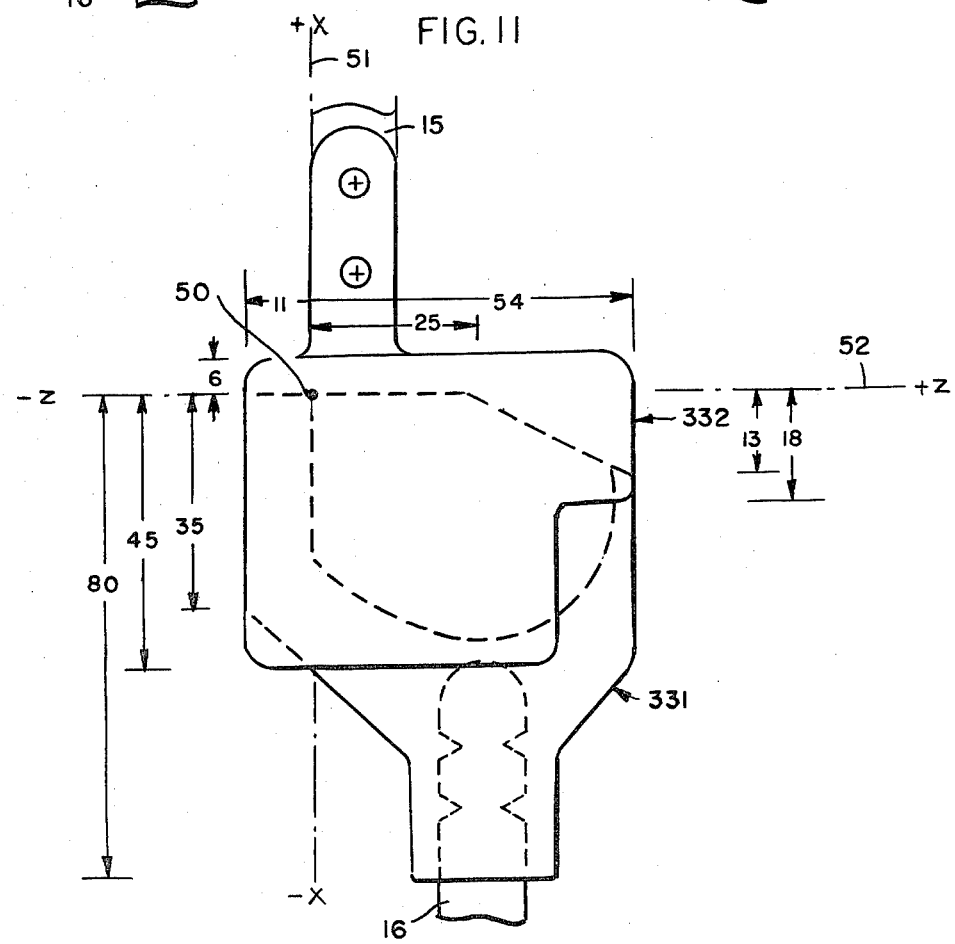

KNEE ORTHOSIS AND JOINT CONSTRUCTION THEREFOR

BACKGROUND

Knee orthoses of various constructions are known and commercially available for protecting knee ligaments as they heal following injuries occuring during athletics or other activities, for bracing the knee where there is chronic instability because of permanent ligament deficiency, for preventing stressing of the knee by a heavy cast worn because of femoral or tibial fracture, or for protecting a wearer pending or in place of surgery for joint repair or replacement. Such orthoses generally represent attempts to provide stability while duplicating the complex actions of the normal knee during flexion and extension. Polycentric or plural-hinge joints have been developed to bring the flexing action of the orthoses into closer conformity with the natural action of the knee but, nevertheless, current devices all have the common disadvantage of constraining normal knee motion because they do not replicate normal knee action. As a result, such orthoses interfere with normal movement, create stresses and loss of stability, tend to slip after a limited period of wear because of constraining forces causing pistoning, and cause skin irritation, patient discomfort, and even pain where the brace bears against bony prominences. In brief, the failure of current orthoses to provide stability while conforming with natural knee movement has greatly reduced the effectiveness of such devices, impaired normal patient movement, and, in extreme cases, caused patient discomfort and/or injury.

Reference may be had to D. Shurr et al, The Iowa Knee Orthosis, Orthotics and Prosthetics, Vol. 32, pp. 20-24 (March 1978) for a discussion of current and prior knee orthoses. U.S. Pat. Nos. 3,902,482, 3,799,159, 4,139,002, and 3,817,244 also reveal the state of the art.

SUMMARY OF THE INVENTION

The orthotic joint of this invention comprises a pair of generally planar guide members having bearing portions of multiple curvatures that roll and slide against each other during knee movement. The interfitting relationship assures stability at all degrees of flexion but there is nevertheless sufficient laxity in the mechanical joint to permit normal action of the patient's knee. The orthotic joint assembly therefore allows the healthy ligaments to control natural knee movement. At the same time, at least one flexible but non-stretchable strap, and ordinarily a plurality of such straps, secured at selected points to the respective members of the orthotic joint, perform essential functions that would normally be performed by the injured or chronically deficient ligament, thereby protecting that ligament without interfering with the functions of the healthy ligaments. The positions and connections of the straps therefore depend on the ligament or ligaments requiring protection or the stability required if such ligament or ligaments are absent. In any case, for any grouping of straps there is a sequential tensioning and untensioning of such straps during flexion and extension, with the result that the injured or deficient ligament is protected at all degrees of flexion.

Briefly, the orthotic knee joint assembly comprises a pair of rigid guide members in the form of a planar femoral member and a tibial member. The femoral member has a head portion with an arcuate bearing surface of varying radii, and the tibial member has a body portion with an open-topped recess slidably receiving the head portion. Within the recess is an arcuate camming surface that engages the bearing surface of the head for guiding movement of the members between extension and flexion. An anchor plate is secured to the femoral member and extends alongside one of the walls of the body portion of the tibial member, and a plurality of flexible, non-stretchable straps have their lower ends secured to the side wall of the tibial member, usually at a common connecting point, and their upper ends secured to the anchor plate at a plurality of different connecting points. Such straps are mounted for sequential tensioning and untensioning as the femoral and tibial members are moved between extension and flexion to create constraints similar to those that would be exerted by a particular ligament, if it were normal, while avoiding exertion of those forces not characteristic of such a ligament. Thus, in the case of an injured ligament, the straps assume the normal function of that ligament and thereby prevent loading of the ligament during the healing process. The net result is that a constraint is available at all joint configurations, but a normal-like joint laxity is available as well.

The femoral member includes an arm portion that projects from the head portion and is adapted to extend alongside a wearer's upper leg, and the tibial member is similarly provided with an arm portion adapted to extend alongside the wearer's lower leg. In a complete orthosis, two such assemblies are provided, and means are also provided for securing the arms of the femoral and tibial members along opposite sides of the wearer's leg above and below the knee joint. Such means may take the form of interfacial connecting members joining a pair of corresponding arm portions of the two assemblies, along with flexible suspension elements or straps for holding the orthosis in position on the wearer's leg. Alternatively, such means may take the form of a cast or casts in which the arm portions of the femoral members, or the arm portions of the tibial members, or both, are embedded.

It has been found that in an orthosis having rigid (or semi-rigid) interfacial members and flexible suspension members, it is important that such members be located at the proximal and distal limits of the orthosis and also at an intermediate location near the head of the tibia. By properly arranging and tensioning the straps at the intermediate location, a three-point or three-zone suspension is provided which effectively maintains the orthotic joints at the proper locations with respect to the natural (or prosthetic) knee joint and, in particular, secures the tibia against anterior or posterior drawer.

Other features, advantages, and objects of the invention will become apparent from the specification and drawings.

DRAWINGS

FIG. 1 is a perspective view of a knee orthosis embodying the present invention.

FIG. 2 is an exploded perspective view illustrating the essential components of an orthotic joint embodying the invention.

FIG. 3 is a side elevational view of the orthotic joint.

FIG. 4 is a front elevational view.

FIG. 5 is a vertical sectional view along line 5—5 of FIG. 3.

FIGS. 6-8 are schematic side elevational views of an orthotic joint for a patient suffering from injury to or deficiency of the posterior cruciate ligament.

FIG. 9 is a side elevational view of the orthotic joint illustrating points of strap connection for a patient with injury to or deficiency of the anterior cruciate ligament.

FIG. 10 is an elevational view similar to FIG. 9 but illustrating points of strap connection for a patient with injury to or deficiency of the collateral ligament.

FIG. 11 is a side elevational view of the joint with straps omitted for clarity of illustration, but with certain dimensions and relationships indicated for the purpose of disclosing details of preferred embodiments of the invention.

DETAILED DESCRIPTION OF PREFERRED EMBODIMENTS

Figure 12:
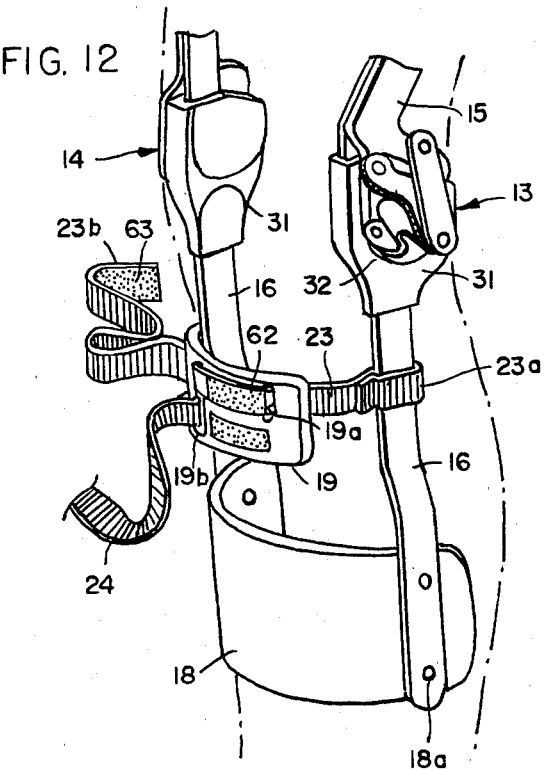
FIG. 12 is a perspective view of a portion of the orthosis showing the initial positioning of the intermediate interfacial member and the associated suspension straps.
Figure 13:
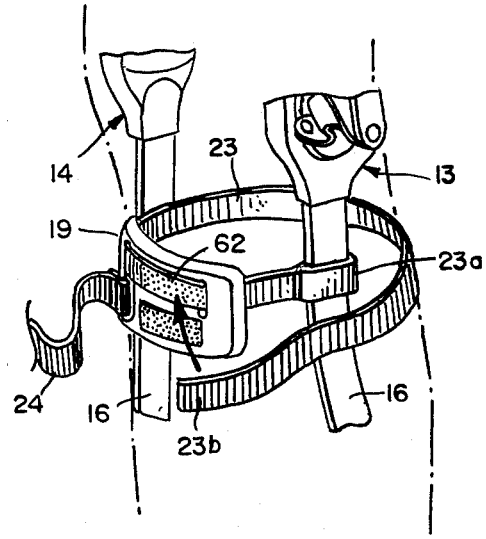
FIG. 13 is a perspective view similar to FIG. 12 but illustrating the manner of attachment of one of the suspension straps.

Referring to FIG. 1, the numeral 10 generally designates a knee orthosis embodying the invention, the orthosis being shown as it might be worn on the left leg 11 of a patient. The orthosis consists essentially of a pair of knee joint assemblies 13 and 14 positioned on opposite sides of the patient's knee 11a, each assembly having arm portions 15 and 16 extending alongside the upper leg 11b and lower leg 11c, respectively, and means for holding the assemblies in such positions. In the embodiment illustrated, such means takes the form of rigid or semi-rigid interfacial members or plates 17, 18, and 19, and suspension members or straps 20, 21, 22, 23, and 24. The upper or proximal plate 17 is shaped to conform the contour of the anterior upper leg 11b and is securely connected to the upper ends of arm portions 15 by means of rivets 17a or any other suitable connecting means. The suspension strap 20 is permanently joined at one end to one of the arm portions and is detachably connected at its other end to the other arm portion or to the outer surface of plate 17 adjacent to that arm portion. Such releasable attachment may be achieved by securing Velcro patches 17b to the overlapping portions of strap 20 and interfacial member or plate 17.

Suspension strap 21 is similarly secured to the upper arm portions 15 of the orthosis. One of the arms may be equipped with an extension plate 25 to provide a greater surface for Velcro patch 25a, and a resilient medial pad or cushion 26 is secured to the opposite arm to insure proper positioning and fit of the orthosis and to increase wearer comfort. The suspension strap 21 works in conjunction with cushion 26 to help immobilize the proximal arms 15 of the orthosis with respect to the femur, thereby complementing interfacial member 17 and suspension strap 20. The thickness of the cushion may be varied to achieve the desired fit and, if desired, the cushion may be removably and/or adjustably mounted upon arm 15. Removable mounting permits interchanging of cushions of different size and shape, an advantage not only in fitting the orthosis to different patients but also in meeting the changing requirements for any given patient. Thus, the growth of a patient's musculature during the healing process may be accommodated by periodically substituting pads 26 of decreasing thickness.

The lower or distal interfacial member or plate 18 is shaped to conform to the contour of the anterior lower leg and is similarly secured to the distal ends of arm portions 16 by rivets 18a. Such rivets also permanently join one end of the suspension strap 22 to one of the arms 16, and Velcro patches 18b releasably join the opposite end of the strap to rigid member 18.

Interfacial member 19 and straps 23 and 24 constitute an intermediate suspension arrangement disposed below joint assemblies 13 and 14 and above the distal interfacial element 18 and strap 22. This intermediate suspension assembly is provided to immobilize the orthotic device with respect to the proximal tibia by serving as a third point of pressure in a three-point pressure suspension system—the other two points being provided by proximal interfacial member 17 and strap 20 (complemented by pad 26 and strap 21) and distal interfacial member 18 and strap 22. As brought out in greater detail hereinafter, straps 23 and 24, and interfacial element 19, are arranged to minimize anterior or posterior drawer of the tibia when the orthoses is used to treat injuries to or deficiencies of the anterior or posterior cruciate ligaments, or of other ligaments such as the collateral ligaments.

The interfacial elements or plates 17, 18, and 19 may be formed of any rigid or semi-rigid material having sufficient strength and durability. Polymethylmethacrylate has been found particularly effective, although other polymeric materials having similar properties may also be used. Furthermore, while the arrangement of interfacial elements and straps shown in the drawings has been found effective for immobilizing proximal arms 15 and distal arms 16 with regard to the femur and tibia, respectively, thereby maintaining joint assemblies 13 and 14 in their proper positions alongside the knee joint, other means for so immobilizing the arms and for locating the joint assemblies might be provided. For example, the upper and lower arms 15 and 16 might be embedded in plaster casts formed about the wearer's leg above and below the knee, as in a case where near-anatomical joint motion is needed to prevent knee damage while a patient recovers from a femoral fracture.

The joint assemblies 13 and 14 on opposite sides of the wearer's leg are basically the same in construction, the main differences being that they are reverse or mirror images of each other, that the arms 15 and 16 may be somewhat different in length and configuration to follow the differences in contour of the wearer's leg, and the guide straps, to be described in detail hereinafter, may be arranged differently, depending upon the particular ligament or ligaments requiring protection or replacement by the orthosis. While the details of only one assembly 13 are shown in FIGS. 2-8, and will be described herein, such detailed disclosure is therefore also applicable to the other assembly 14.

Each orthotic joint assembly includes four main components: a femoral member 30, a tibial member 31, an anchor plate 32, and guide straps 33. The femoral member 30 is planar and includes, as an integral portion thereof, the upstanding elongated proximal arm portion 15 previously described (FIG. 2). In addition, the femoral member has at its lower end an enlarged head portion 34. The head portion has an arcuate bearing surface 35 of varying radii of curvature with the posterior portion 35a of that surface having smaller radii of curvature than the anterior portion 35b thereof. In general, the curvature of bearing surface 35 simulates or conforms to the curvature of a femoral condyle viewed in sagittal section. It will be noted, however, that the leading or anterior portion 35c of the bearing surface is substantially straight and constitutes an extension of the leading edge of arm portion 15. The arm portion is provided with openings 36 at its upper end for receiving rivets 17a and, in addition, is provided with threaded openings 37 directly above head portion 34. While the femoral member 30 may be formed of any strong, rigid, and durable material, it is believed that a light-weight metal such as aluminum is particularly effective.

The head portion 34 of the femoral member 30 is received with an upwardly-facing recess 38 provided by tibial member 31 (FIG. 2). Recess 38 has a narrow arcuate camming surface 39 that, when viewed in outline, corresponds closely to the curvature of bearing surface 35 (FIG. 3). Maximum contact between such surfaces occurs when the members are in extension (FIGS. 3 and 6). In that condition of close conformity, with the substantially straight leading surface 35c of the femoral head portion abutting the substantially straight anterior portion 39a of the camming surface 39, the femoral and tibial members are restrained against both hyperextension and posterior-anterior sliding translation. Because the curvature of the posterior portion 35a of the arcuate femoral bearing surface 35 is of smaller radii than that of the anterior portion 35b thereof, the extent of contact between bearing surface 35 and camming surface 39 decreases during flexion (FIGS. 7, 8). As the degree of flexion increases, the more limited contact between the bearing and camming surfaces, and the decreased anterior-posterior dimension of the head portion 34 in relation to that of recess 38, allows limited anterior-posterior sliding movement of the head portion within the recess, at least in the absence of some natural or artificial constraining means. Thus, referring to FIG. 8, in the absence of some constraining means, head portion 34 would be free to slide anteriorly a limited distance within recess 38 until its curved anterior surface engages the straight anterior surface 39a of the recess.

The tibial member 31 includes both the recess-providing body portion 40 and the depending or distal arm portion 16. The two portions may be formed integrally of the same rigid material, although it is believed preferable to fabricate body portion 40 from a rigid polymeric material such as polypropylene or a polypropylene-polyethylene copolymer (90%/10% formulation has been found effective) and to embed the upper end of arm 16, formed of aluminum or other material having similar properties, within the body portion as indicated. In any event, the body portion includes a pair of planar side walls 41 and 42 that are spaced apart to define the narrow recess 38 and that are merged together in front of, below, and behind such recess to define the narrow camming surface 39 within that recess (FIGS. 2, 5). The spacing between the opposing faces of walls 41-42 is the same as, or only slightly greater than, the width of the head portion 34 of femoral member 30; therefore, when the parts are assembled a coplanar relationship is maintained with the planar surfaces of the head portion being in sliding engagement with the planar surfaces within the recess.

Anchor plate 32 extends alongside, and in planar relation with, wall 42 of the body portion of tibial member 31 (FIGS. 4, 5). The rigid anchor plate, formed of aluminum or any other material having similar properties of strength, rigidity, and durability, has an upstanding connection portion 43 joined to the arm portion 15 of femoral member 30. Screws 44 are shown for that purpose; however, other means for rigidly securing the anchor plate to the femoral member, such as riveting or welding, may also be used.

A plurality of guide straps 33a, 33b, and 33c are shown joining the tibial member 31 and anchor plate 32. The straps are flexible but essentially non-stretchable. They may be formed of woven metal, glass, or synthetic or natural fibers. Dacron fabric has been used effectively. It will be observed that the straps are apertured at their ends and are secured by rivets or other suitable connecting means to both the tibial member and the anchor plate, with ordinarily only a single rivet 45 joining the lower ends of all three straps to the tibial member at a common point (opening 45a), and with three rivets 46-48 joining the opposite ends of the straps to the anchor plate at three different connecting points (openings 46a, 47a, and 48a). For convenience, such rivets and the openings in which they are located will be referred to as the points of attachment 45-48 of straps 33a-33c.

The straps function to exert forces similar to those that would be exerted by a particular ligament such as, for example, the posterior cruciate ligament, throughout the full range of knee movement. At least three such straps would normally be required—one to function in extension, another to function at approximately 90° flexion, and a third to function at approximately 45° flexion. If greater control is deemed necesary, a greater number of straps may be provided in each set or, in certain circumstances, a fewer number of straps may suffice. The straps operate sequentially rather than simultaneously; when one strap is fully tensioned, the others are untensioned. More specifically, when the knee is full extension, only the posterior strap 33c is fully tensioned, when the knee is at 90° flexion only the anterior strap 33a is tensioned and, at an intermediate position, only the intermediate strap 33b is fully tensioned.

The points of attachment of the straps and, hence, the length and orientation of each strap, must be precisely determined on the basis of the normal functioning of the particular ligament to be protected or reinforced. For purposes of illustration, FIGS. 1-5 (also 6-8) illustrate the attachment and positioning of straps for a patient with injury to or chronic deficiency of the posterior cruciate ligament. Because of the complexity of the functioning of a normal knee joint, with rolling, sliding, and spinning of the femoral condyles relative to the tibial surfaces, and with changing centers of rotation combined with sliding displacement of the articular surfaces, there has been considerable misunderstanding and contradiction in the past concerning knee joint ligament mechanics. Such mechanics are now better understood because of recent studies by applicants and others (see Lew, W. D., and J. L. Lewis, A Technique for Calculating In Vivo Ligament Lengths with Application to the Human Knee Joint, J. Biomechanics, Vol. 11, pp. 365-377 (1978)). For purposes of this disclosure, it is believed sufficient to state simply that the posterior cruciate ligament normally functions to pull the head of the femur in a posterior or rearward direction over the tibial articular surface during flexion and to hold it in a rearward position when the knee is fully flexed. Actual forces in the ligaments will depend on the external loads applied to the joint. The articulation of femoral member 30 and tibial member 31 of the orthotic joint mimics the articulation of the natural joint, and the set of straps 33 is mounted to exert forces during flexion, as well as at extension and 90° flexion, that mimic forces that would normally be exerted by a natural posterior cruciate ligament.

Such functioning is illustrated somewhat schematically in FIGS. 6-8. In those views, for clarity of illustration, the straps 33 as such are not shown and a solid heavy line is used to schematically represent only the particular strap under tension at the illustrated position of knee movement. Thus, FIG. 6 corresponds to FIG. 3 but illustrates that strap 33c, extending between attachment points 45 and 46, is the only strap fully tensioned when the orthotic joint (and the natural knee with which the orthosis is associated) is locked in extension. At 45° flexion (FIG. 7), only the intermediate strap 33b extending between attachment points 45 and 47 is fully tensioned, and at 90° flexion (FIG. 8) only the strap 33a between points 45 and 48 is tensioned. If it were not for straps 33a and 33b, the head 34 of the femoral member would be free to slide forwardly within recess 38 because of the decreasing radii of curvature of the posterior portion of the femoral head. Therefore, when the orthotic joint as shown is part of a complete orthosis worn by a patient because of injury to or deficiency of the posterior cruciate ligament, the straps function sequentially to perform major functions of the natural posterior cruciate ligament, thereby protecting that ligament, without at the same time interfering with any natural movements of the knee and, in fact, without supplanting the functions of major ligaments other than the posterior cruciate. To illustrate the latter, it will be noted from FIG. 8 that strap 33a exerts a downward and rearward force that would not necessarily prevent the head portion 34 of the femoral member from being lifted slightly within recess 38; however, in the natural knee such a function is performed by the collateral ligaments and, assuming the patient has no injury or deficiency with respect to his collateral ligaments, those ligaments are allowed to perform their functions without any duplication or reinforcement by the orthosis.

For a patient whose condition requires protection of other major ligaments, the straps and their points of attachment would be different. FIG. 9, for example, depicts an orthotic joint for use with a patient having an injured or chronically deficient anterior cruciate ligament. Apart from the straps and their points of attachment, the joint shown is the same as already described except for slight differences in the outlines of anchor plate 132 and the head portion 140 of tibial member 131. The three straps that would extend between the common attachment point 145 and the three different connecting points 146-148 are omitted for clarity of illustration, but it will be understood that, as in the previous embodiment, the posterior strap bridging attachment points 145 and 146 would be the only strap tensioned when the joint is in extension, the anterior strap bridging attachment points 145 and 148 would be the only one fully tensioned when the joint is in 90° flexion, and the intermediate strap bridging points 145 and 147 would be the only strap fully tensioned when the joint is in 45° flexion. The plurality of straps would thus function sequentially to exert forces similar to those of a natural anterior cruciate ligament; that is, the straps would urge the head portion 34 of the femoral member forwardly and downwardly during flexion and extension.

FIG. 10 illustrates a joint with strap attachment points arranged for protection of a collateral ligament. Again, the joint is the same as already described except for the differences in the attachment points and minor differences in the outline of anchor plate 232 and tibial body portion 231. The straps are omitted, but the posterior strap would extend between attachment points 245 and 246, the intermediate strap between points 245 and 247, and the anterior strap between points 245 and 248. Sequential tensioning of the straps would occur as before but in this case the straps would exert forces similar to those of a natural collateral ligament. Specifically, the straps would act sequentially to exert forces tending to prevent vertical separation of the parts. Thus, bearing surface 35 of the femoral head portion is maintained in sliding contact with camming surface 39 of the tibial body by successive action of the guide straps.

FIG. 11 is a generalized view of an orthotic joint, exclusive of straps and connections, that is identical to the joints already described except for differences in the outlines of the anchor plate 332 and tibial body portion 331. The numeral 50 designates a reference point at the intersection of x and z axes 51 and 52, respectively. The configuration and dimensions (in millimeters) of the anchor plate and tibial body portion are sufficient to provide for the strap attachment points for protecting any of the three major ligaments (collateral, anterior cruciate, posterior cruciate) as well as other ligaments of secondary importance. Reference may be had to the following table for the coordinates along axes x and z, measured in millimeters from point 50, for strap attachments for treating or protecting major ligaments:

| | Table of Strap Attachment Points (mm) (along with x and z coordinates, respectively) | | | |
|---|---|---|---|---|
| Ligament | Common Point (45,145,245) | Post. Point (46,146,246) | Int. Point (47,147,247) | Ant. Point (48,148,248) |
| Posterior Cruciate | 41,48 | 2,33 | 10,−3 | 37,13 |
| Anterior Cruciate | 32,−7 | 9,45 | 2,33 | 10,10 |
| Collateral | 48,26 | 2,33 | 3,9 | 27,12 |

Major dimensions of the components are given in FIG. 11. The angular outlines of the anchor plate 332 and tibial body portion 331 are provided primarily for dimensional reference, it being understood that in an actual orthosis it would be preferable to round off the corners of the parts to a greater extent (as in FIGS. 1-8) to remove unused material, avoid interference, and promote greater patient comfort.

It is to be understood that many other strap placements are possible, depending on the specific ligamentous problem, and that strap placement will vary from those given in the case of total knee joint replacement. In the case of injury or deficiency of the posterior cruciate, anterior cruciate, or collateral ligaments, the straps would ordinarily be joined to the tibial member at a common connecting point (e.g., 45, 145, 245); however, where an orthotic joint is designed to protect more than one ligament, or where unusual knee injuries or conditions are presented, or where the natural joint has been replaced by a prosthesis that typically does not replicate normal knee movement, such straps may be connected to the tibial member at more than one connecting point. Also, while the orthotic joint would normally be equipped with a plurality of straps that are tensioned sequentially during flexion, it is possible that a patient's condition may require the joint to have only a single strap; for example, a strap that is tensioned in extension simply to prevent hyperextension of the natural joint. The straps have been disclosed as flexible but inextensible, and it is believed that inextensibility is essential for effective operation of the orthotic joint. Such inextensibility does not, however, preclude the possibility that each strap might be composed of sections that are buckled together to provide a composite strap of the precise length necessary for the purpose it is intended to serve. Thus, the straps might be of adjustable length for proper fitting of the orthosis by a physician or therapist and then, when buckled or otherwise set at their prescribed lengths, such straps would become inextensible for wearing of the orthosis by the patient.

Figure 17:
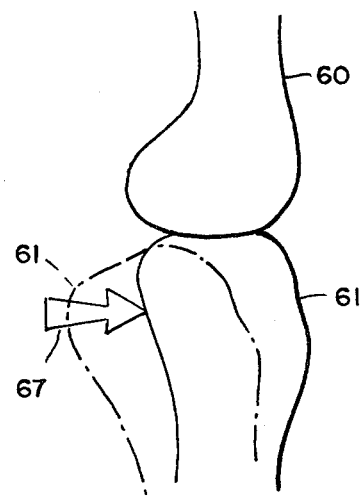
FIG. 17 is a schematic view illustrating the tibial drawer prevented by the arrangement of straps and interfacial elements depicted in FIG. 16.
Figure 19:
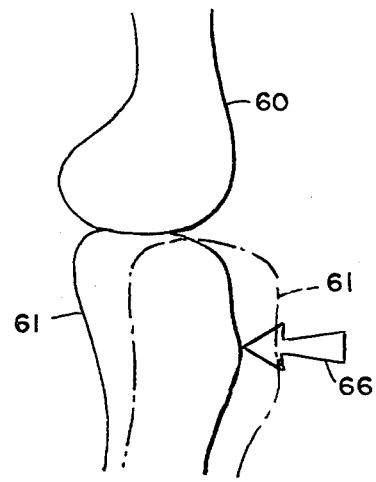

FIGS. 12–15 depict the steps of attaching the intermediate suspension means that serves to immobilize arms 16, and the tibial members 31 to which they are joined, with respect to the patient's tibia. Such intermediate suspension thereby prevents or restrains anterior or posterior tibia drawer. FIG. 17 schematically depicts a knee joint with femur 60 and tibia 61 in extension. Posterior drawer, represented in broken lines, is posterior displacement of the tibial head because of the absence or deficiency of the natural posterior cruciate ligament. Similarly, the broken lines in FIG. 19 depict anterior tibial drawer resulting from the absence or deficiency of the anterior cruciate ligament. While the orthotic joints 13 and 14 of this invention are designed to prevent such anterior or posterior drawer (depending on the arrangement of straps associated with such joints), the orthotic joints are capable of preventing such action only if the arms 16 of the tibial members 31 are immobilized in relation to the tibial head.

Figure 14:
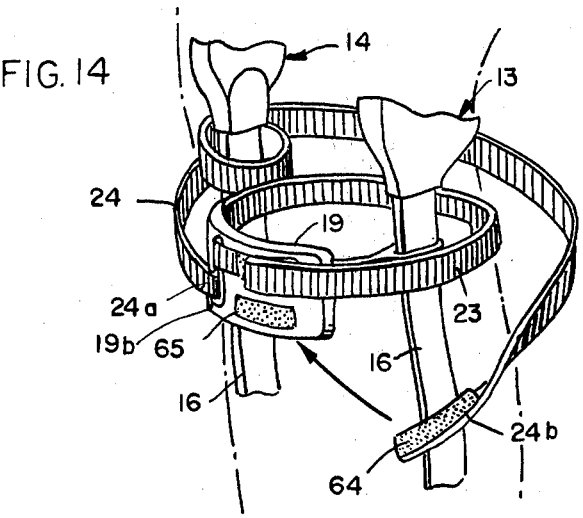
FIG. 14 illustrates the manner of attachment of a second suspension strap.
Figure 15:
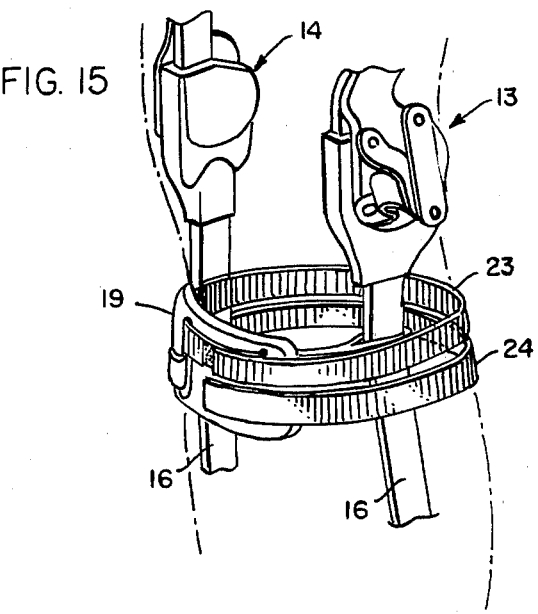
FIG. 15 depicts the intermediate interfacial member and straps after attachment thereof is completed.

FIGS. 12–15 illustrate the straping arrangement for preventing anterior drawer. Strap 23 has one of its ends 23a secured to one of the arms 16. The strap passes through slots 19a and 19b in interfacial member or plate 19, with the portion of the strap along the outer surface of the member 19 being provided with Velcro strip 62. The opposite end 23b of the strap is provided with a mating Velcro patch 63. The strap is extended about the wearer's leg inboard of the arm 16 associated with joint 14 and outboard of the arm for joint 13, and the Velcro patch at 23b is then brought into contact with patch 62 in the manner illustrated in FIG. 13. Strap 24 has one end 24a secured to interfacial member 19 at slot 19b and, as shown in FIG. 14, is wrapped about the arm 16 associated with orthotic joint 14. The strap 24 then continues about the posterior portion of the leg and its end 24b is secured to interfacial element 19 by means of Velcro patches 64 and 65. The suspension, when completed, appears as depicted in FIG. 15. Strap member 23 functions primarily to prevent anterior (and posterior) displacement of the tibial head with respect to arm 16 associated with joint assembly 13, and strap member 24 functions primarily to immobilize the tibial head with regard to arm 16 of joint assembly 14. The arcuate member or plate 19 acts as the interface between the suspension straps and the anterior portion of the wearer's leg to help brace the leg against the possibility of tibial drawer. It is believed apparent that this intermediate suspension assembly operates in conjunction with the lower suspension assembly (composed of interfacial member 18 and strap 22), and also in conjunction with upper suspension assembly (comprising interfacial member 17, straps 20 and 21, and pad 26) to provide a third pressure zone in an essentially three-point suspension arrangement.

Figure 16:
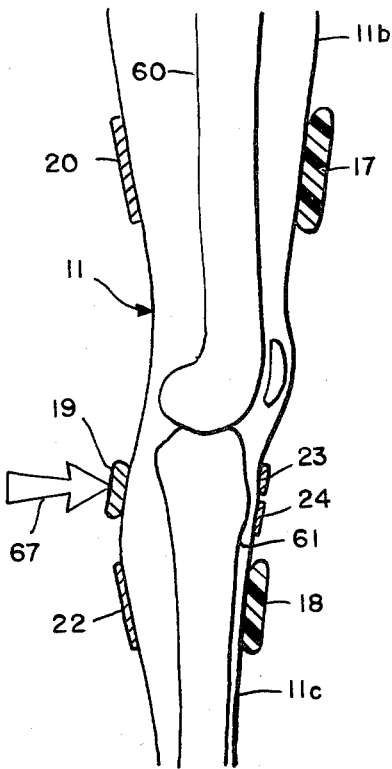
FIG. 16 is a somewhat schematic sagittal view of the leg showing the preferred arrangement of interfacial members and suspension straps for a patient with an injured posterior cruciate ligament.
Figure 18:
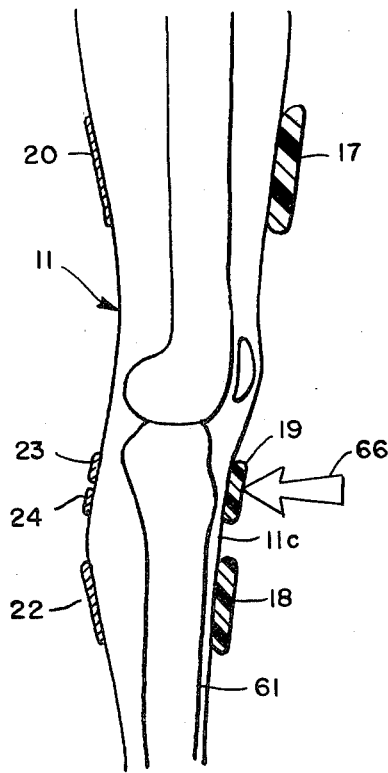
FIGS. 18 and 19 are somewhat schematic views similar to FIGS. 16 and 17 but illustrating the arrangement of interfacial elements and straps for treating a patient with an injured anterior cruciate ligament, and the anterior drawer which such an arrangement prevents.

The relationship is schematically depicted in FIG. 18 where it will be seen that interfacial element 19 exerts a posteriorly-directed force represented by arrow 66 to prevent anterior tibial drawer (FIG. 19). The intermediate suspension would also function (when so needed) to prevent posterior tibial drawer; however, it is believed desirable, for more effective use of the intermediate suspension system, to locate interfacial element 19 posteriorly of the patient's leg (FIG. 16) when posterior drawer is to be prevented. A resultant force is then directed anteriorly by interfacial element 19 as represented by arrow 67. Except for the change in location of interfacial element 19, the intermediate suspension of FIG. 16 is essentially as described in connection with FIGS. 12–15.

While in the foregoing we have disclosed embodiments of the invention in considerable detail for purposes of illustration, it will be understood by those skilled in the art that many of these details may be varied without departing from the spirit and scope of the invention.

I claim:

1. An orthotic knee joint assembly comprising a rigid planar femoral member having a head portion with a narrow arcuate bearing surface of varying radii of curvature and having an arm portion projecting from said head portion and adapted to extend upwardly alongside a wearer's upper leg; a rigid tibial member having a body portion and an arm portion adapted to extend downwardly alongside a wearer's lower leg; said body portion having a pair of planar side walls spaced apart to define a narrow open-topped recess slidably receiving said head portion and having an arcuate camming surface engaging said bearing surface for guiding movement of said members between extension and flexion along constantly changing instantaneous axes of rotation, said bearing surface being slidable posteriorly and anteriorly along said camming surface when said members are in flexion; a rigid anchor plate extending alongside one of said side walls and having a connecting portion secured to said arm portion of said femoral member; and at least one flexible and non-stretchable strap having a lower end secured to said one side wall at a selected connecting point and having an upper end secured to said anchor plate at another selected connecting point; said strap being mounted for tensioning and untensioning as said members are moved between extension and flexion to exert a force for guiding said bearing surface with respect to said camming surface during articulation of a patient's knee.

2. The assembly of claim 1 in which said head portion has its planar surfaces in sliding engagement with the surfaces of said side walls of said body portion within said recess to permit movement of said members only in a sagittal plane.

3. The assembly of claim 1 in which said arcuate camming surface of said tibial member is generally congruent with the arcuate bearing surface of said femoral member when said members are in extension.

4. The assembly of claim 3 in which said camming and bearing surfaces also include substantially straight anterior portions that are disposed in abutting relation when said members are in extension.

5. The assembly of claim 1 in which one of said head and body portions is formed of rigid polymeric material and the other is formed of rigid metal.

6. The assembly of claim 5 in which said body portion of said tibial member is formed of polymeric material.

7. The assembly of claim 5 in which said head portion of said femoral member is formed of metal.

8. The assembly of claims 5, 6, or 7 in which said anchor plate is formed of metal.

9. The assembly of claim 1 in which a plurality of said straps are provided; said straps being mounted for sequential tensioning and untensioning as said members are moved between flexion and extension.

10. The assembly of claim 9 in which said straps have their lower ends secured to said anchor plate at a common connecting point.

11. The assembly of claim 10 in which said common connecting point is located adjacent the posterior edge of said one wall and said straps are sequentially tensioned and relaxed to exert forces similar to a natural posterior cruciate ligament as said members are moved between flexion and extension.

12. The assembly of claim 10 in which said common connecting point is located adjacent the anterior edge of said one wall and said straps are sequentially tensioned and relaxed to exert forces similar to a natural anterior cruciate ligament as said members are moved between flexion and extension.

13. The assembly of claim 10 in which said common connecting point is located approximately midway between the anterior and posterior limits of said one wall and said straps are sequentially tensioned and relaxed to exert forces similar to natural collateral ligaments as said members are moved between flexion and extension.

14. The assembly of claim 1 in which said assembly is a component of a complete knee orthosis; said orthosis including a second assembly similar to said first-mentioned assembly; means for securing the arm portions of said femoral members along opposite sides of a patient's upper leg; and means for securing the arm portions of said tibial members along opposite sides of a patient's lower leg.

15. The orthosis of claim 14 in which at least one of said means comprises a cast in which the arm portions secured thereto are embedded.

16. The orthosis of claim 14 in which at least one of said means comprises an interfacial member adapted to be connected to a pair of corresponding arm portions of said assemblies and curved to conform with the contour of a portion of the patient's leg; and at least one strap member secured to said interfacial member and adapted to extend about the leg for immobilizing said arm portions with respect thereto.

17. The orthosis of claim 14 in which said first-mentioned means includes a first interfacial member connected to said femoral arm portions and shaped to extend anteriorly across the upper leg of a wearer; strap means for detachably securing said first interfacial member against the upper leg; said second-mentioned means including a second interfacial member connected to said tibial arm portions and shaped to extend anteriorly across the lower leg of a wearer; strap means for detachably securing said second interfacial member against the lower leg; and a third interfacial member adapted to engage the lower leg at a point spaced above said second interfacial member and directly below a wearer's knee; said third interfacial member being equipped with strap means engaging said tibial arm portions and adapted to extend about the upper portion of a wearer's lower leg to prevent tibial drawer.

18. The orthosis of claim 17 in which said interfacial members are formed of rigid material.

19. An orthotic knee joint assembly comprising a rigid planar femoral member having a head portion with a narrow arcuate polycentric bearing surface and having an arm portion projecting from said head portion and adapted to extend upwardly alongside a wearer's upper leg; a rigid tibial member having a body portion and an arm portion adapted to extend downwardly alongside a wearer's lower leg; said body portion having a pair of planar side walls spaced apart to define a narrow open-topped recess receiving said head portion and having an arcuate camming surface engaging said bearing surface for guiding movement of said members between extension and flexion along constantly changing instantaneous axes of rotation, said bearing surface being slidable posteriorly and anteriorly along said camming surface when said members are in flexion and being generally congruent with said camming surface when said members are in extension; said head portion also having its planar surfaces in slidable engagement with the opposing surfaces of said side walls of said body portion within said recess; a rigid anchor plate extending alongside one of said side walls and having a connecting portion secured to said arm portion of said femoral member; and a plurality of flexible non-stretchable guide straps having lower ends secured to said tibial member at at least one connecting point and having upper ends secured to said anchor plate at a plurality of connecting points; said straps being mounted for sequential tensioning and untensioning as said members are moved between extension and flexion to exert forces similar to those that would be exerted by a selected normal knee ligament during external loading while avoiding the exertion of forces not associated with such ligament that might constrain knee joint articulation.

20. The assembly of claim 19 in which said camming and bearing surfaces also include substantially straight anterior portions that are disposed in abutting relation when said members are in extension.

21. The assembly of claim 19 in which one of said head and body portions is formed of rigid polymeric material and the other is formed of rigid metal.

22. The assembly of claim 21 in which said body portion of said tibial member is formed of polymeric material.

23. The assembly of claim 21 in which said head portion of said femoral member is formed of polymeric material.

24. The assembly of claims 21, 22, or 23 in which said anchor plate is formed of metal.

25. The assembly of claim 19 in which said non-stretchable guide straps have their lower ends secured to said tibial member at a single common connecting point.

26. The assembly of claim 25 in which said common connecting point is located adjacent the posterior edge of said end wall and said straps are sequentially tensioned and relaxed to exert forces similar to a natural posterior cruciate ligament as said members are moved between flexion and extension.

27. The assembly of claim 25 in which said common connecting point is located adjacent the anterior edge of said one wall and said straps are sequentially tensioned and relaxed to exert forces similar to a natural anterior cruciate ligament as said members are moved between flexion and extension.

28. The assembly of claim 25 in which said common connecting point is located approximately midway between the anterior and posterior limits of said one wall and said straps are sequentially tensioned and relaxed to exert forces similar to a natural collateral ligament as said members are moved between flexion and extension.

29. The assembly of claims 19, 25, 26, 27, or 28 in which said assembly is a component of a complete knee orthosis; said orthosis including a second assembly similar to the first-mentioned assembly; means for securing the arm portions of said femoral members to each other along opposite sides of a patient's upper leg; and means for securing the arm portions of said tibial members to each other along opposite sides of a patient's lower leg.

30. The orthosis of claim 29 in which at least one of said means comprises a cast in which the arm portions secured thereto are embedded.

31. The orthosis of claim 29 in which said first-mentioned means includes a first interfacial member connected to said femoral arm portions and shaped to extend anteriorly across the upper leg of a wearer; strap means for detachably securing said first interfacial member against the upper leg; said second-mentioned means including a second interfacial member connected to said tibial arm portions and shaped to extend anteriorly across the lower leg of a wearer; strap means for detachably securing said second interfacial member against the lower leg; and a third interfacial member adapted to engage the lower leg at a point spaced above said second interfacial member and directly below a wearer's knee; said third interfacial member being equipped with strap means engaging said tibial arm portions and adapted to extend about the upper portion of a wearer's lower leg to prevent tibial drawer.

32. The orthosis of claim 31 in which said interfacial members are formed of rigid polymeric material.

33. A knee orthosis comprising a pair of hinge assemblies adapted to be disposed on opposite sides of a wearer's knee, each hinge assembly including an upper arm portion adapted to extend upwardly alongside the wearer's upper leg and a lower arm portion adapted to extend downwardly alongside the wearer's lower leg; said hinge assemblies having constantly changing instantaneous axes of rotation as said upper and lower arm portions are moved between extension and flexion; means for securing said upper arm portions along opposite sides of a wearer's upper leg, said means including a first interfacial member connected to said upper arm portions and shaped to extend anteriorly across the upper leg of a wearer, and strap means for detachably securing said first interfacial member against the upper leg; and means for securing said lower arm portions along opposite sides of a wearer's lower leg, said second-mentioned means including a second interfacial member connected to said lower arm portions and shaped to extend anteriorly across the lower leg of a wearer, strap means for detachably securing said second interfacial member against the lower leg, and a third interfacial member adapted to engage the lower leg at a point spaced above said second interfacial member and directly below a wearer's knee, said third interfacial member being equipped with strap means engaging said lower arm portions and adapted to extend about the upper portion of a wearer's lower leg to prevent tibial drawer.

34. The orthosis of claim 33 in which said interfacial members are formed of rigid polymeric material.

35. The orthosis of claim 33 in which each hinge assembly includes a femoral member secured to said arm portion and having an arcuate bearing surface, and a tibial member secured to said lower arm portion and having an arcuate camming surface slidably and rotatably engaging said bearing surface.

36. The orthosis of claim 33 in which each of said hinge assemblies also includes at least one guide strap secured at one end to said femoral member and at its other end to said tibial member for guiding movement of said bearing surface along said camming surface.

* * * * *